United States Patent
Taheri (12)

(10) Patent No.: US 6,620,095 B2
(45) Date of Patent: Sep. 16, 2003

(54) CRADLE-ASSISTED MYOCARDIAL REPAIR AND TREATMENT

(76) Inventor: Syde A. Taheri, 1275 Delaware Ave., Buffalo, NY (US) 14209

( * ) Notice: Subject to any disclaimer, the term of this patent is extended or adjusted under 35 U.S.C. 154(b) by 59 days.

(21) Appl. No.: 09/747,792

(22) Filed: Dec. 22, 2000

(65) Prior Publication Data

US 2002/0082469 A1 Jun. 27, 2002

(51) Int. Cl.⁷ .................................................. A61F 2/00
(52) U.S. Cl. ............................................. 600/37; 600/16
(58) Field of Search ....................... 600/37, 16

(56) References Cited

U.S. PATENT DOCUMENTS 6,293,906 B1 * 9/2001 Vanden Hoek et al. ....... 600/37

* cited by examiner

Primary Examiner—Noah P. Kamen
(74) Attorney, Agent, or Firm—Walter W. Duft

(57) ABSTRACT

A cradle apparatus for myocardial repair and treatment includes a cradle having a base end and an open end. A lumen extends to a location which is at or near the cradle's base end. A plurality of spring arms are mounted to the lumen and attached to the open end of the cradle. The spring arms are biased to apply an opening force to the open end of the cradle such that the cradle apparatus can be compacted into a percutaneous or transarterial introducer and then expanded upon emergence from the introducer to engage a ventricular wall of a heart. The cradle is adapted to apply a myocardial repair or treatment material, such as myocyte cells, medicines and like, to a dysfunctional myocardium. A balloon cradle apparatus is also disclosed for myocardial treatment via an endocardial approach.

7 Claims, 18 Drawing Sheets

CRADLE-ASSISTED MYOCARDIAL REPAIR AND TREATMENT

STATEMENT REGARDING FEDERALLY SPONSORED RESEARCH OR DEVELOPMENT

Not Applicable

CROSS-REFERENCE TO RELATED APPLICATIONS

Not Applicable

BACKGROUND OF THE INVENTION

1. Field of the Invention

This invention relates to cardio myopathy and the treatment thereof.

2. Description of the Prior Art

By way of background, cardio myopathy, as caused for example by myocardial infarction, is a common disorder. Twenty thousand new cases are reported yearly in the United States and 25–50% of such cases will result in death after three years. The problem is that damaged adult heart muscle does not regenerate and myocardial functionality cannot be restored using the body's natural healing mechanisms. The myocardium tends to dilate and areas of the ventricular walls may become hypokinetic, or even akinetic, such that congestive heart failure often develops in affected individuals.

Previous medical techniques have not substantially reduced the morbidity or mortality of this condition. Past efforts in this area include removing autologous muscle cells, stem cells, etc., and culturing them to generate the large number of implantation cells necessary for myocardial repair. The cultured cells are then implanted via injection into the myocardium, where they have an opportunity to regenerate new heart muscle. Applicant has previously proposed a cell patch method whereby autologous muscle grafts are applied to damaged myocardial tissue. See U.S. Pat. No. 5,327,913. According to this method, the muscle grafts are placed against a patient's outer myocardial wall and a section of the patient's greater omentum is applied over the grafts to supply blood to the transplanted tissue. In a recently developed improvement of the cell patch method, a percutaneous procedure is used to secure the muscle grafts to the myocardium. Applicant has also recently proposed a microgranule treatment wherein autologous myocyte microgranules are injected into a patient's inner or outer myocardial wall using an injection needle introduced via a transfemoral or surgical approach.

Evaluation of these previous treatment proposals suggests a need for a more efficient method of applying myocyte donor material to the myocardium. For example, a cell patch method that did not require the suturing of muscle grafts would greatly simplify and expedite a cell patch procedure. Similarly, a cultured cell or micro-granule injection treatment that did not require repeated individual injections would greatly improve the implementation of such procedures. A new apparatus and method for myocardial repair and treatment is therefore indicated.

SUMMARY OF THE INVENTION

The foregoing problems are solved and an advance in the art is obtained by a novel cradle apparatus for autologous myocardial repair and treatment. The cradle apparatus includes a cradle having a base end and an open end, and is adapted to apply a myocardial repair or treatment material to a dysfunctional myocardium. A lumen extends to a location which is at or near a base end of the cradle. In two disclosed embodiments of the cradle, a plurality of spring arms are mounted to the lumen and also attach to the open end of the cradle. The spring arms are biased to apply an opening force to the open end of the cradle, whereby the cradle apparatus can be compacted into a percutaneous or transarterial introducer and then expanded upon emergence from the introducer to engage a ventricular wall of a heart. In particular, the cradle apparatus can be adapted to be twisted and compacted inside the introducer, which will typically be generally tubular in shape.

The spring arms can be made from metal and the lumen is adapted to receive one or more instruments, including a suction cup mounted to a hydraulic sheath that extends through the lumen. This instrument is used to elevate the apex of a heart to receive the cradle apparatus.

In accordance with a first one of the foregoing embodiments, the cradle is configured as a prosthesis for holding a material against a myocardium. In that case, the cradle includes a constrictor at its open end and is removably attached to the spring arms. According to a second one of the foregoing embodiments, the cradle is configured for applying a material into or on a myocardium via a pericardial approach. In that case, the cradle includes a double-walled inflatable bladder having a system of needles on one wall thereof adapted to dispense the material.

A third embodiment is also disclosed wherein the cradle apparatus does not utilize spring arms. In this embodiment, the cradle is configured for applying a material into or on a myocardium (or a coronary arterial wall) via an endocardial approach. The cradle includes an inflatable balloon having a system of needles adapted to dispense the material.

A combination of the cradle configurations may likewise be employed in accordance with the invention. For example, the cradle apparatus may include first and second cradles. The first cradle is configured for applying a material into or on a myocardium via a pericardial approach, and includes a double-walled inflatable bladder having a system of needles on one wall thereof adapted to dispense the material. The second cradle is configured for applying a material into or on a myocardium (or coronary arterial wall) via an endocardial approach, and includes an inflatable balloon having a system of needles adapted to dispense the material.

BRIEF DESCRIPTION OF THE DRAWING

The foregoing and other features and advantages of the invention will be apparent from the following more particular description of preferred embodiments of the invention, as illustrated in the accompanying Drawing, in which.

DETAILED DESCRIPTION OF THE PREFERRED EMBODIMENT

The preferred embodiments of the novel cradle apparatus of the invention will now be described by way of several exemplary embodiments. These embodiments include two cradle apparatus that can be introduced percutaneously and used to externally cover a patient's ventricular walls, and a third cradle apparatus that can be inserted via an artery and fed into a ventricular chamber or coronary arterial wall. Collectively, the disclosed cradle apparatus allow injection or application of myocyte cells, myocyte granules and drugs into the myocardium, and further allow the application of autologous muscle graft patches and cell packs directly or selectively onto myocardial tissue.

Figure 1:
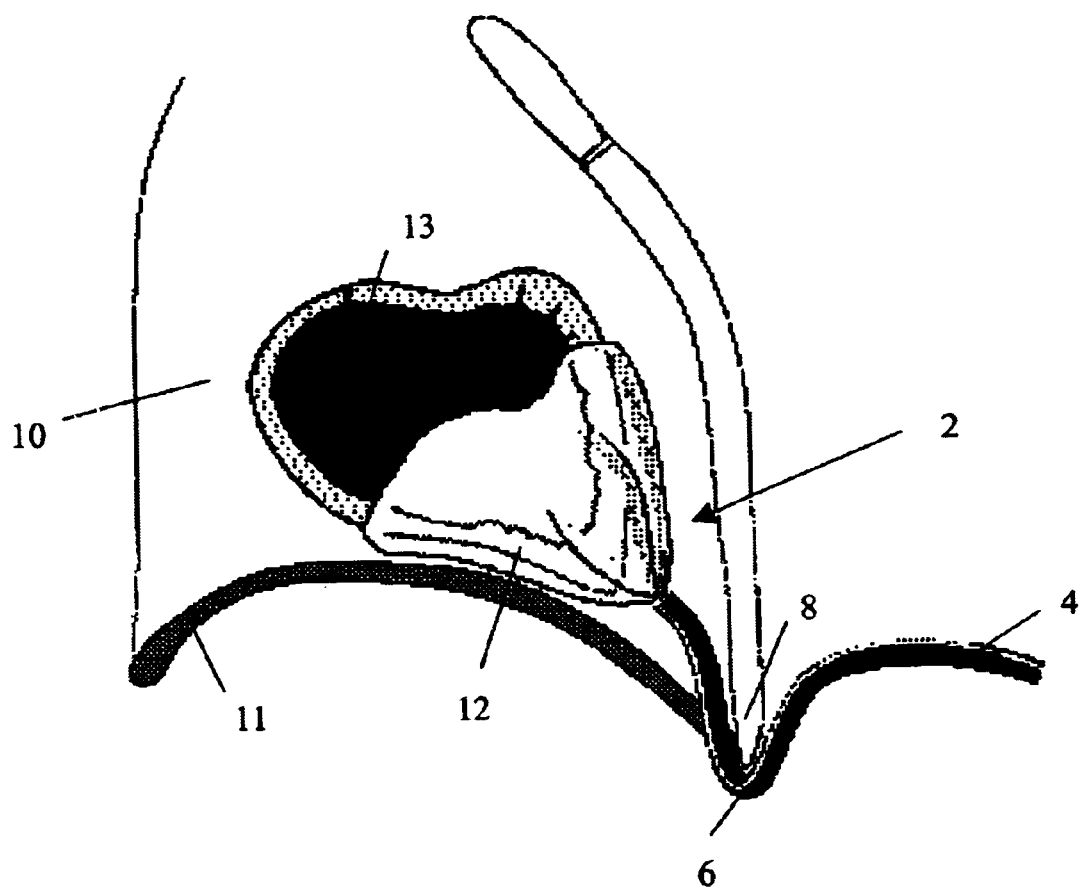
FIG. 1 is a diagrammatic side elevation view of the interior of a patient's chest cavity showing percutaneous introduction using a xiphoidal approach of a cradle apparatus constructed in accordance with a first embodiment of the invention.
Figures 2, 4:
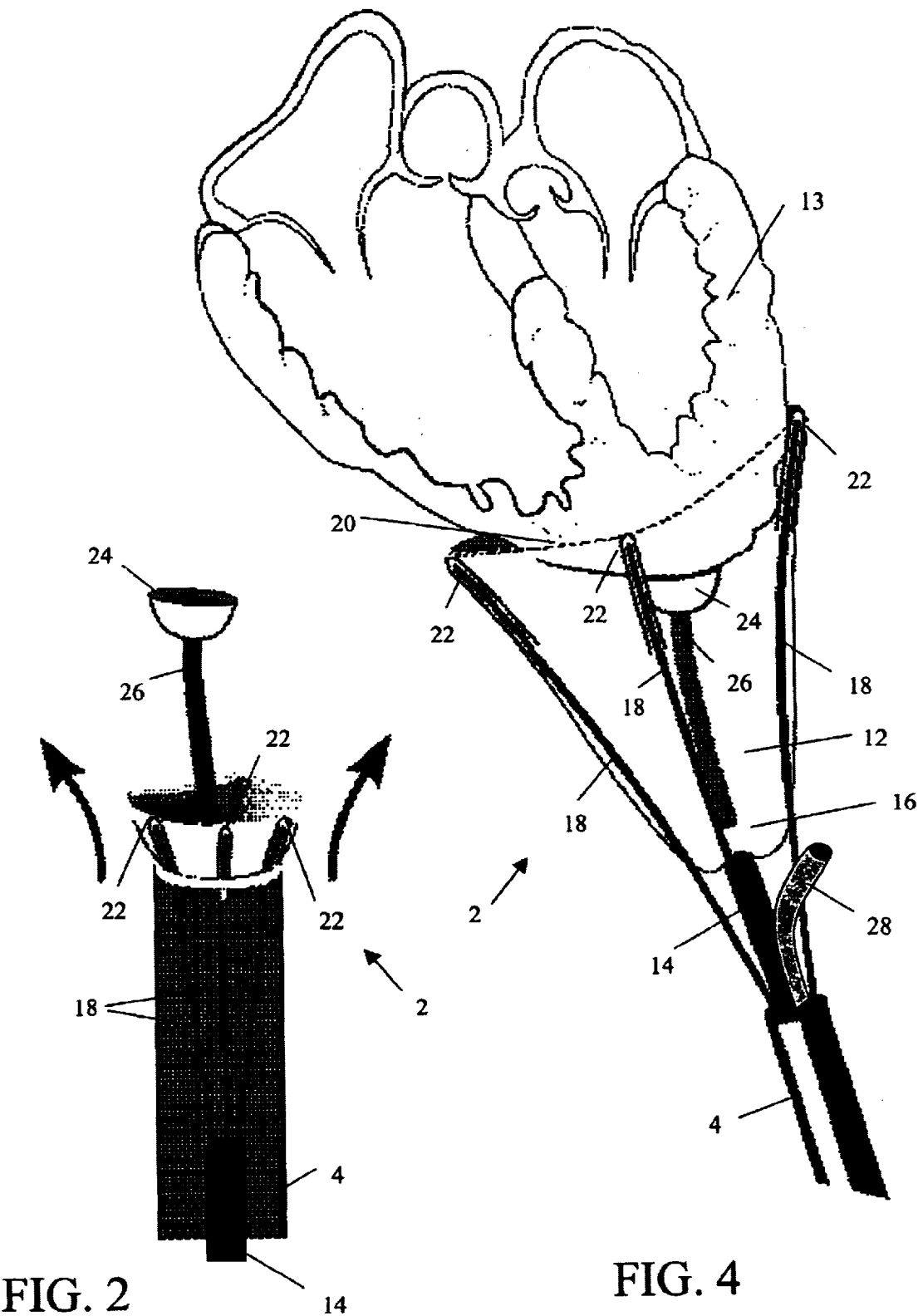
FIG. 2 is an enlarged partial perspective view showing the cradle apparatus of FIG. 1 emerging from a percutaneous introducer.
FIG. 4 is a perspective view showing the cradle apparatus of FIG. 1 extended from the introducer of FIG. 2 and enveloping a patient's ventricular walls.
Figure 3:
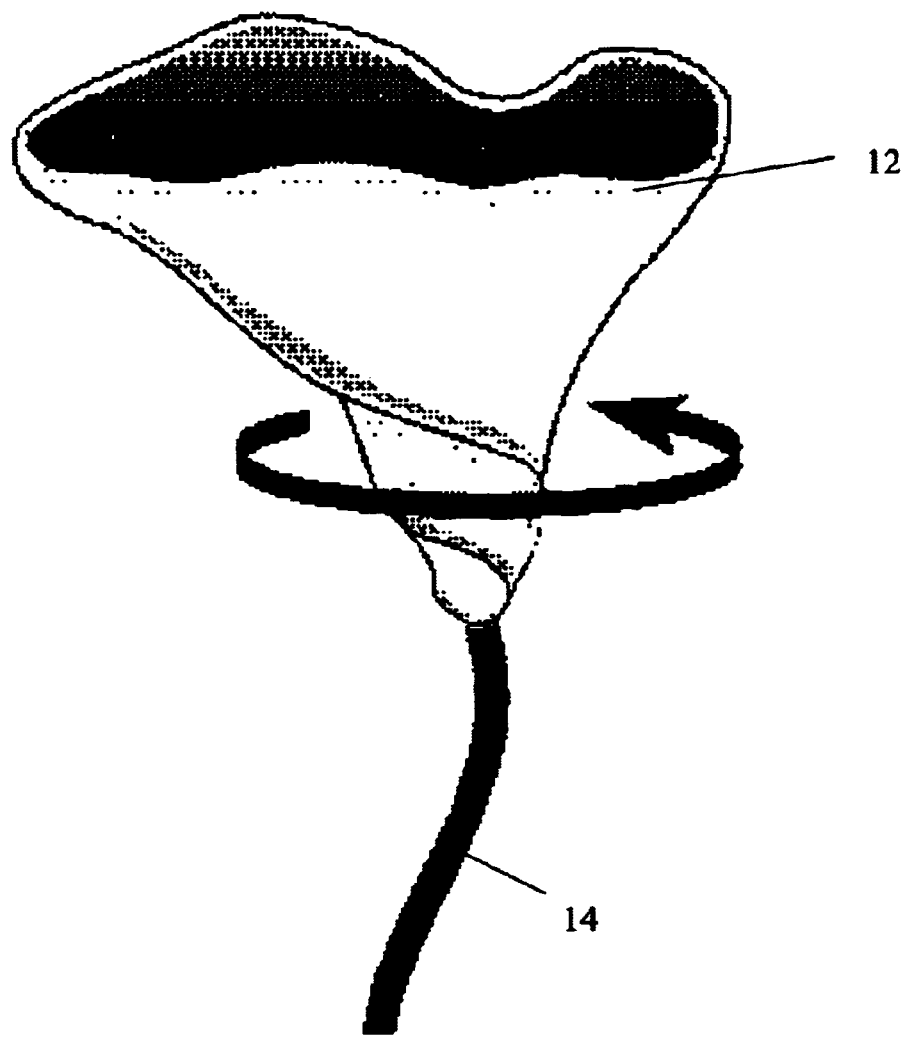
FIG. 3 is a perspective view showing the cradle apparatus of FIG. 1 being untwisted for deployment after emerging from the introducer.

1. Non-Inflatable Cradle Apparatus for Percutaneous Procedures Using Pericardial Approach Turning now to FIG. 1, a cradle apparatus 2 extends from an introducer 4 that has been inserted through an opening 6 below a patient's xiphoid bone 8 and into the patient's pericardium 10, above the diaphragm 11. The cradle apparatus 2 includes a cradle 12 that covers the right and left ventricles of the patient's heart 13. FIGS. 2–4 illustrate the cradle apparatus 2 in more detail. In FIG. 2, the cradle apparatus 2 is shown as it emerges from the introducer 4. In FIG. 3, the cradle apparatus 2 is shown being untwisted for deployment following its emergence from the introducer 4. In FIG. 4, the cradle apparatus 2 is fully deployed and in the process of being positioned around the right and left ventricles.

In addition to the cradle 12, the cradle apparatus 2 includes a lumen 14 that extends to a location which is at or near the cradle's terminal end 16. In particular, the terminal end of the lumen 14 could be connected to the base end 16, could extend beyond it, or could terminate short of it. The cradle apparatus 2 further includes a plurality of spring arms 18. The spring arms 18 are mounted to the lumen 14 and extend to the cradle's open end 20, where they are received in pockets 22. The lumen 14 is sized so that it can receive implements or materials. The former could include a hydraulic suction cup 24 mounted at the end of a hydraulic sheath 26. As described in more detail below, this arrangement is used to elevate the heart to receive the cradle 12. Other implements would include video and echo imaging probes. Materials that can be carried by the lumen 14 include gasses, such as $CO_2$, and liquid materials, such as myocyte injection compositions, drugs, saline (for cradle inflation), etc.

A variety of materials can be used to fabricate the foregoing components. The introducer 4, for example, can be made from any suitably flexible material, such as braided steel sheathing or prosthetic material. By way of example only, a 25 french introducer may be used for a xiphoidal approach. The cradle 12 can be made from any suitable sheet material that is appropriate for surgical use. Depending on the application for which the cradle apparatus 2 will be used (see below), the cradle 12 could be made from a fluid impervious material, such as plastic, or a single-walled absorbable or prosthetic material, such as Vicryl® absorbable suture material. Regardless of the material used, the cradle may be generally cup-shaped, as shown in FIGS. 1–14, or balloon shaped, as shown in FIGS. 15–20. In either case, the cradle will include an intermediate wall portion extending between its two ends. The lumen 14 can be made from any suitable stiff yet flexible material, such as plastic tubing. The spring arms 18 can be made from any suitable material that exerts an outward spring force. Examples include thin nitinol (nickel-titanium alloy) bars that are preloaded to open outwardly and untwist (if the cradle apparatus 2 was previously twisted) once the cradle apparatus emerges from the introducer 4. A cantilevered attachment of the spring arms 18 to the lumen 14 should provide a suitable anchor for the spring arm forces.

Percutaneous introduction of the cradle apparatus 2 entails preparing the opening 6 below the patient's xiphoid bone using local anesthesia and routine preparation. The introducer 4, with the suction cup 24 and hydraulic sheath 26 disposed therein, is introduced into the pericardium 10. Advancement of the suction cup 24 and hydraulic sheath 26 while manipulating the introducer 4 brings the suction cup into contact with the ventricular apex of the heart 14 (see FIG. 4). Suction is now applied to elevate the heart as necessary. The cradle apparatus 2 is then compressed and twisted so that it fits within the introducer 4. It, along with the lumen 14, are then passed over the outside hydraulic sheath 26 and advanced until the cradle 12 begins emerging from the distal end of the introducer 4, as shown in FIG. 2. Further advancement of the lumen 14 pushes the cradle 12 fully out of the introducer 4 where it begins to untwist by virtue of the spring arms 18, as shown in FIG. 4. Once the cradle apparatus 2 is fully open, as shown in FIG. 3, the lumen 14 is further advanced until the cradle 12 covers the ventricular walls of the heart 13.

3. Diastolic Cardio-Therapy

The cradle apparatus 2 can be used for diastolic cardio-therapy. In accordance with this method, a suction tube 28 is fed through the introducer 4 and hydraulic suction is applied to the pericardium 10. To seal the pericardium 10, an inflatable bladder (not shown) can be used to occlude the opening 6. Suction is applied to the tube 28 on a periodic basis. In particular, suction is applied during the heart's diastolic phase and released during the heart's systolic phase. This results in a massaging action that assists the heart to draw more blood volume into the ventricles during the diastolic phase, and consequently pump more blood volume out of the ventricles during the systolic phase. As part of this procedure, a viewing device, such as a video camera or echo imaging probe (not shown), can be passed through the introducer and used to observe ventricular function.

Note that adjustable rate and cycle controls, along with pressurization controls, may be used to fine tune the cardio-therapy treatment being provided, making this method adaptable to the needs of many different patients. A further benefit of the method is that it is non-thrombotic. This is in contrast to current cardio-therapy methods wherein blood pumps are introduced into a patient's blood vessels. Anti-coagulants, such as Heparin, are therefore unnecessary.

2. Cradle Patch Cardio-Myoplasty

Figures 5, 6:
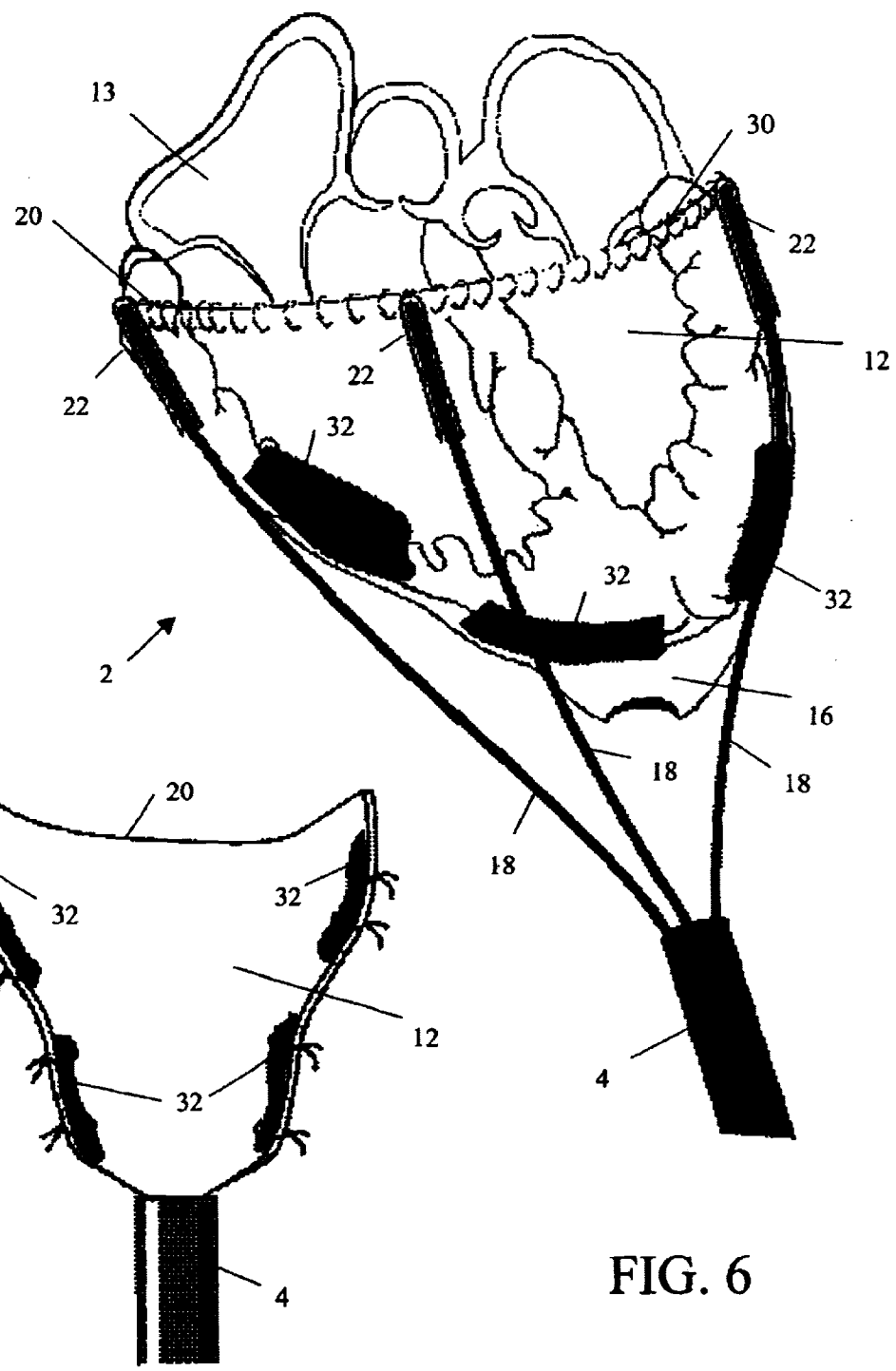
FIG. 5 is a partial cross-sectional view taken along a central vertical axis of the cradle of apparatus of FIG. 1 and showing autologous muscle grafts secured thereto to form a prosthesis for positioning the muscle grafts in engagement with a patient's heart.
FIG. 6 is a perspective view showing the cradle apparatus of FIG. 5 extended from the introducer of FIG. 5 and enveloping a patient's ventricular walls.
Figure 7:
FIG. 7 is a side elevation view showing a spring element received in a spring element mounting pocket formed as part of the prosthesis of FIG. 5.
Figure 8:
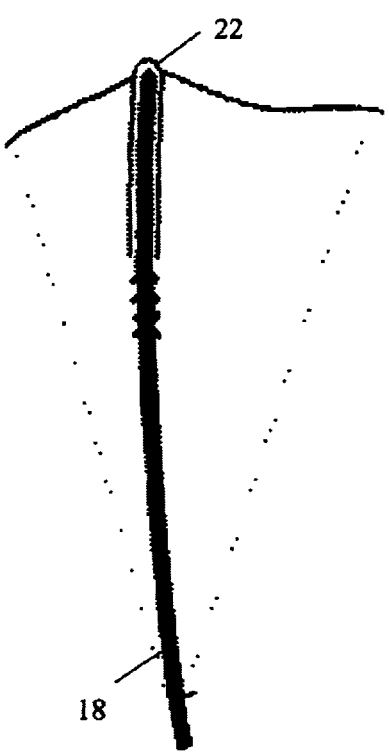
FIG. 8 is a front elevation view showing a spring element received in a spring element mounting pocket formed as part of the prosthesis of FIG. 5.
Figure 9:
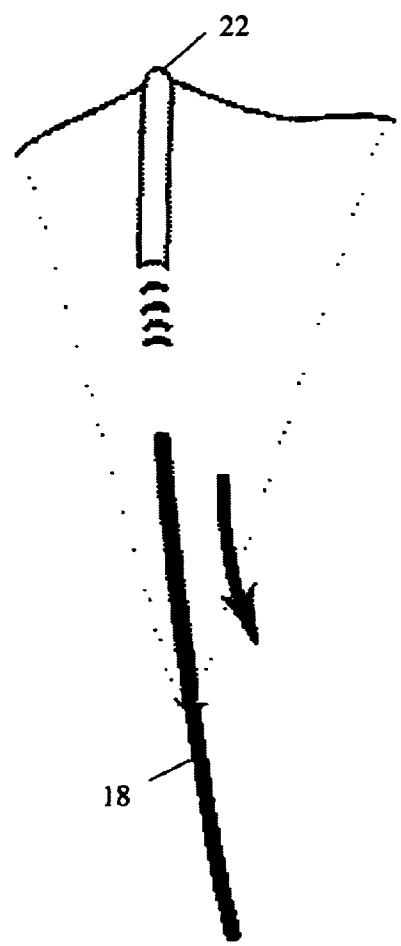
FIG. 9 is a front elevation view showing removal of a spring element from a spring element mounting pocket formed as part of the prosthesis of FIG. 5.

Turning now to FIGS. 5–6, the cradle apparatus 2 can be modified to perform cradle patch cardio-myoplasty. In this configuration, the cradle 12 comprises a sheet of absorbable or prosthetic material. Associated with its terminal end 20 is a tie, band or other constrictor 30 that exerts a closing force on the terminal end. This closing force, though present, is not of sufficient magnitude to prevent the spring arms 18 from opening the cradle 12 when the cradle apparatus 2 emerges from the introducer 4. An additional design modification that needs to be made to the cradle apparatus 2 is to provide for detachment of the spring arms 18 from the pockets 22, as shown in FIGS. 7–9. Moreover, the cradle 12 should not be connected to the lumen 14.

In accordance with the cradle patch cardio-myoplasty method described herein, the cradle 12 serves as a prosthesis that mounts a plurality of autologous cell patches 32 along the cradle's inner wall. The cell patches 32 can be secured to the cradle 12 (e.g., using absorbable sutures) shortly before commencement of the procedure. Once the cell patches 32 are so mounted, the cradle apparatus 2 is introduced into the pericardium 10 and advanced until the cradle 12 covers the ventricular walls of the heart 13 in the manner described above. At this point, as shown in FIGS. 7–9, the spring arms 18 are retracted from the pockets 22 by carefully withdrawing the lumen 14 from the introducer 4. As the spring arms 18 are pulled out of engagement with the cradle 12, the force of the constrictor 30 closes the open end 20 of the cradle, causing the cradle to secure itself in position on the heart 13. In this position, the cell patches 30 will be firmly pressed against the outer myocardial wall, and will have an opportunity to become incorporated therein via the body's natural healing mechanisms to form functioning myocardial tissue. The cradle 12 can be subsequently removed by re-entering the pericardium 10, releasing the constrictor 30, and retrieving the cradle through an introducer. Alternatively, the cradle 12 (and the constrictor 30) could be made from an absorbable material, such as Vicryl® absorbable suture material.

Note that an alternative to the foregoing procedure could be implemented wherein, instead of using cell patches, small bags (e.g. 1–2 cm long) made of dissolvable material and containing cultured cells are mounted to the cradle 12. As the bags dissolve, the cultured cells will come into contact with the myocardium and have an opportunity to incorporate themselves therein as functioning myocardial tissue.

3. Inflatable Cradle for Mycardial Treatment Via Pericardial Approach

Turning now to FIGS. 10–14, the cradle apparatus 2 can be modified to treat the myocardium with cultured cells, myocyte micro-granules, medicines, and the like. In this configuration, the cradle 12 comprises a bladder 40 formed by a double wall of fluid-impervious sheet material, such as plastic. The bladder 40 has an outer wall 42 and an inner wall 44. An end wall 46 of the bladder 40 defines the cradle's terminal end 20. At or near the cradle's point of attachment to the lumen 14, the bladder 40 is adapted at 48 to receive fluid from a suitable source of pressuring fluid, such as the lumen 14 or a separate hydraulic fluid line (not shown).

Figures 10, 10A:
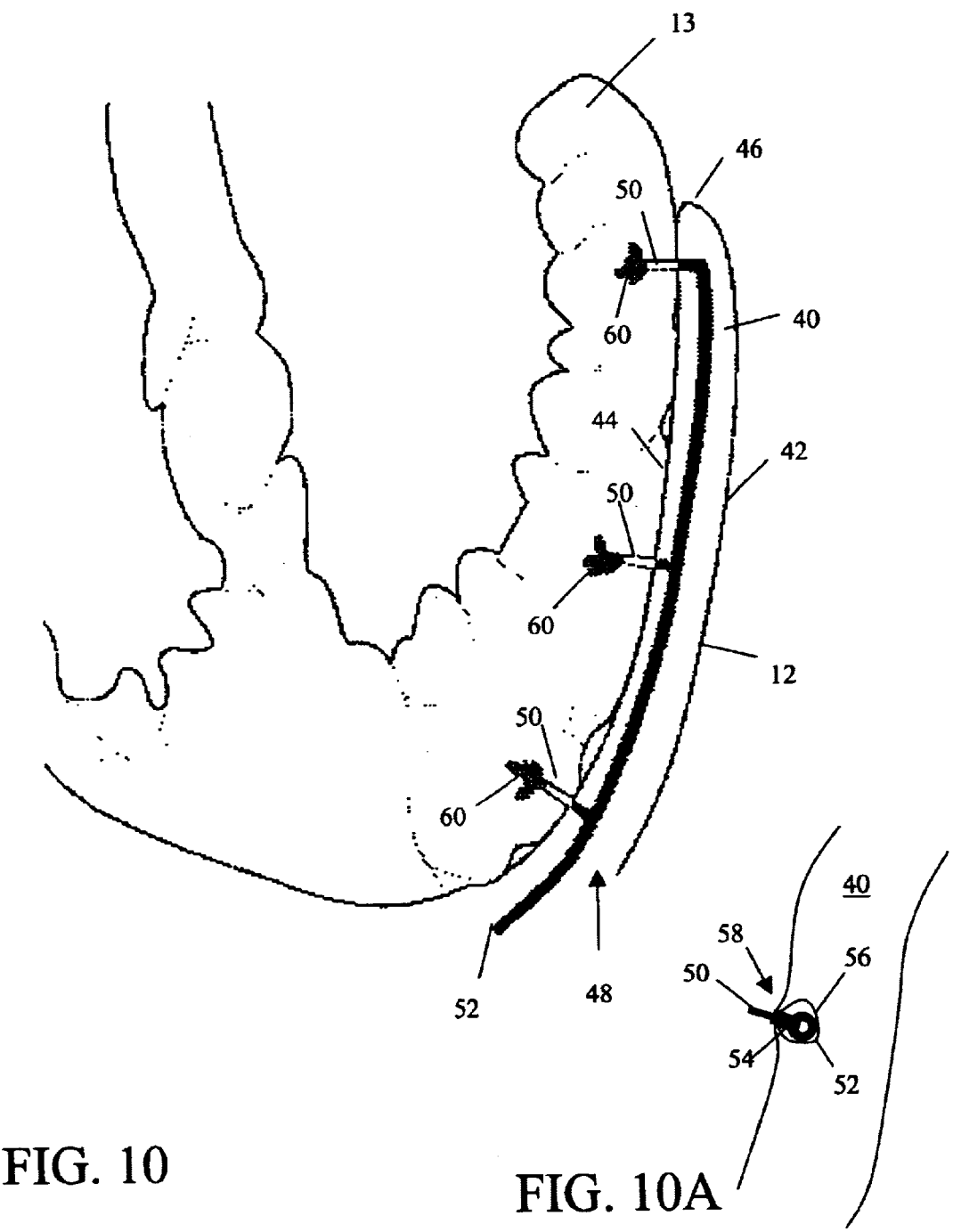
FIG. 10 is a partial cross-sectional view of an inflatable cradle apparatus constructed according to a second embodiment of the invention, wherein the cradle is adapted to carry a plurality injection needles and is shown contacting a patient's ventricular walls with the injection needles commencing the injection of material into the myocardium.
FIG. 10A is detailed cross-sectional view showing an alternative construction of the cradle apparatus of FIG. 10.

The cradle apparatus 2 further includes a plurality of short injection needles 50, made from stainless steel or the like, that can be on the order of a millimeter in length. Each injection needle 50 is supplied by an injection tube 52 having branches 54 that each lead to one or several of the injection needles. One such injection tube 52 is shown in FIG. 10. Other injection tubes of like construction would supply injection needles located at other areas of the cradle 12. It will be seen that the injection tube 52 and branches 54 shown in FIG. 10 lie within the bladder 40, and that the injection needles extend through the inner wall 44. In an alternative configuration, shown in FIG. 10A, a longitudinal slot 56 is formed in the surface of the inner wall 44 that is adapted to face the myocardial wall. The function of the longitudinal slot 56 is to slidably receive the injection tube 52. The longitudinal slot 56 thus preferably has a substantially circular cross-sectional shape and is sized to snugly receive the injection tube 52. Pinched openings 58 are provided to cover the injection needles 50 prior to bladder inflation. The openings 58 are designed to retract to expose the injection needles 50 when the bladder is pressurized.

Figure 11:
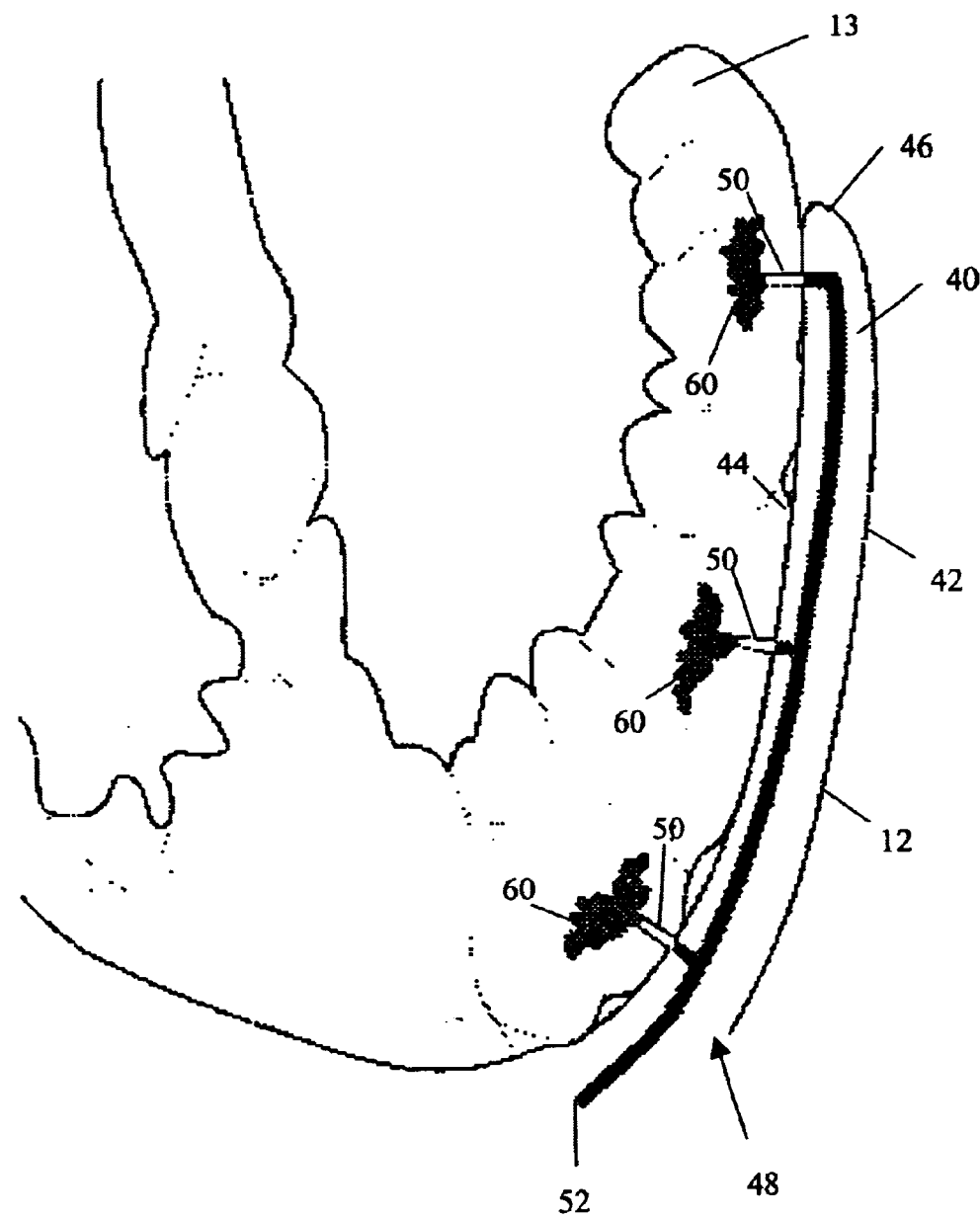
FIG. 11 is another partial cross-sectional view similar to FIG. 10 but with the injection needles completing the injection of material into the myocardium.
Figure 12:
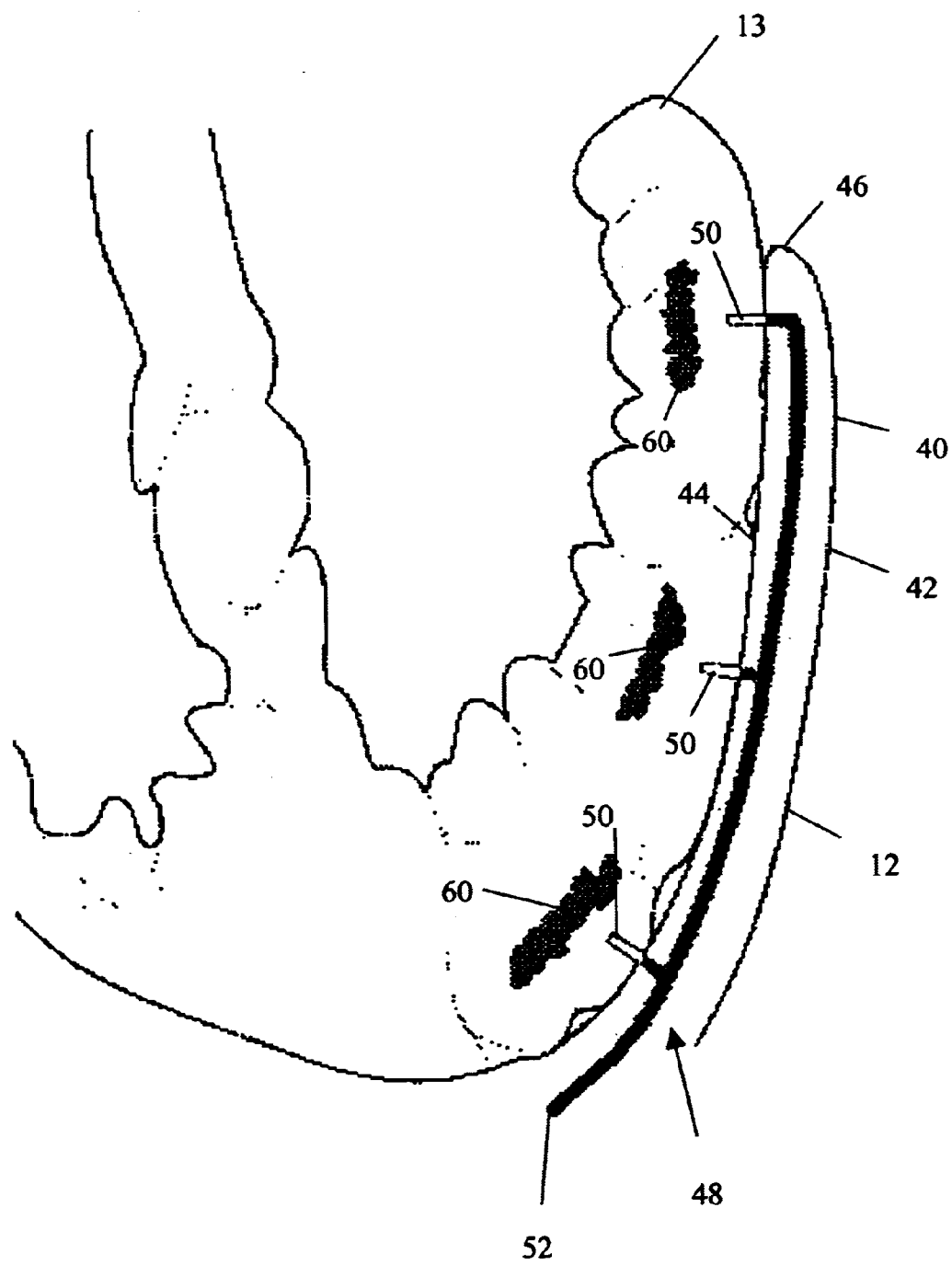
FIG. 12 is another partial cross-sectional view similar to FIG. 10 but with the injection needles being removed after injecting material into the myocardium.
Figure 13:
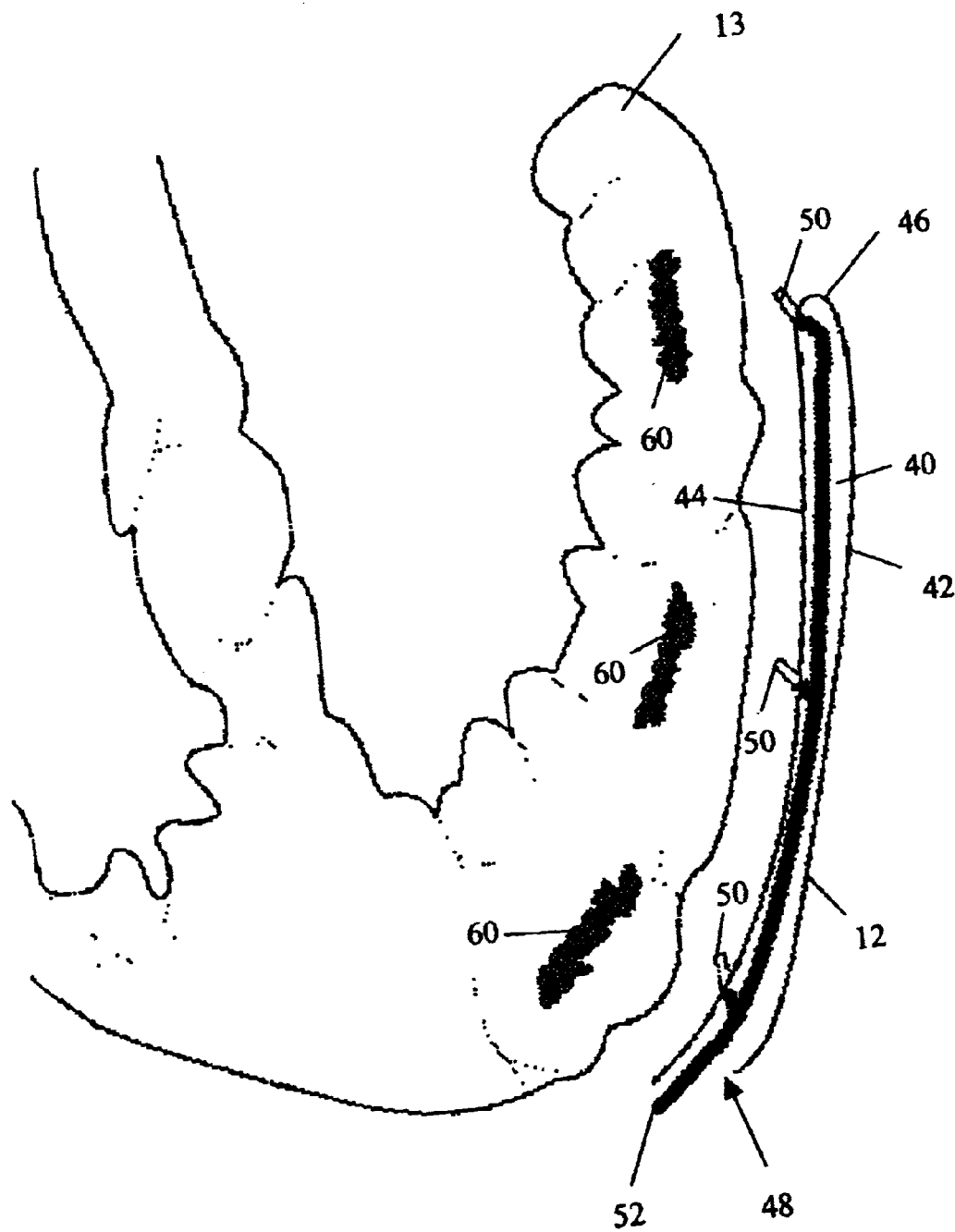
FIG. 13 is another partial cross-sectional view similar to FIG. 10, but with the cradle in an initial stage of retraction away from a patient's heart following the injection of material into the myocardium.
Figure 14:
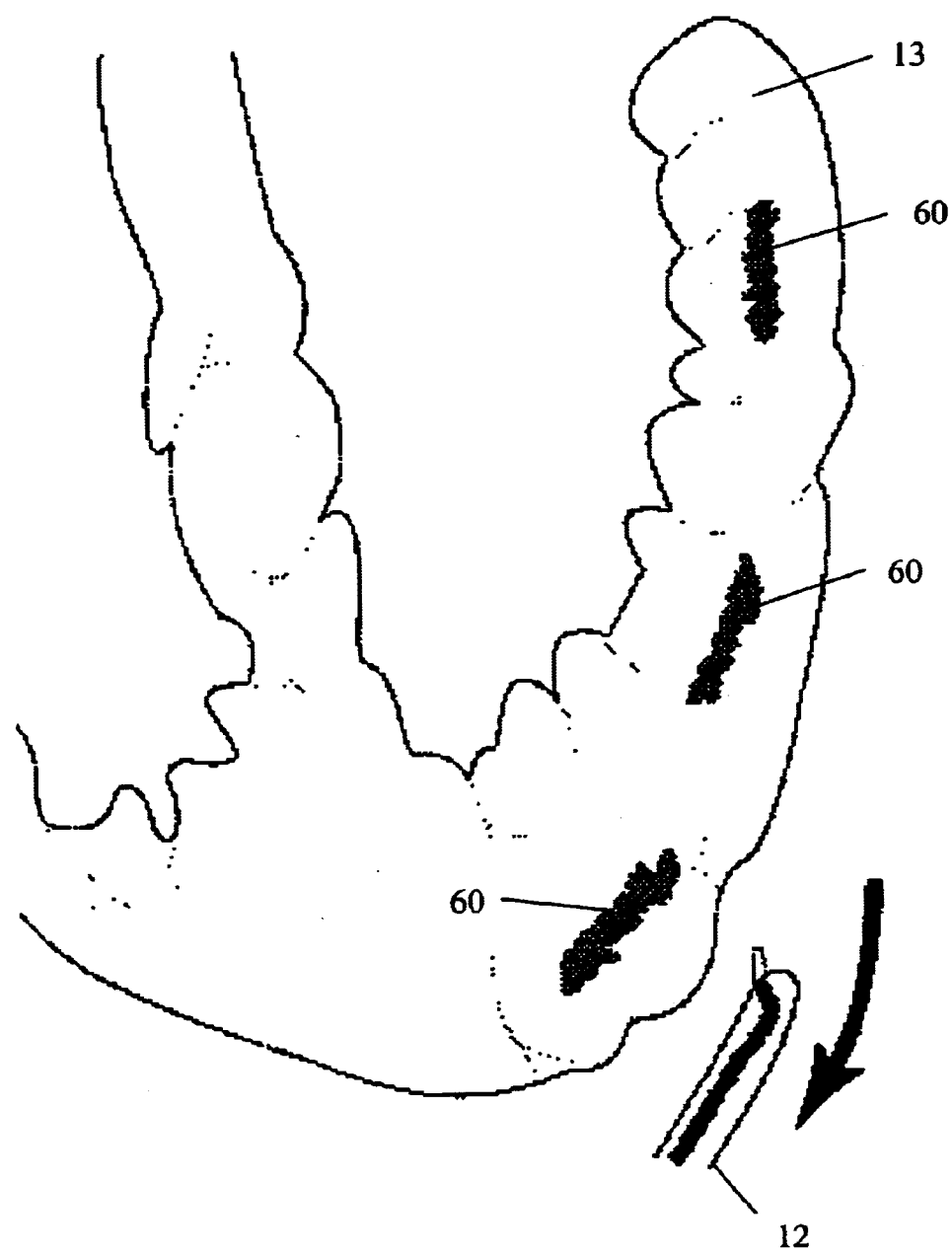
FIG. 14 is another partial cross-sectional view similar to FIG. 10 but with the cradle in an advanced stage of retraction away from a patient's heart following the injection of material into the myocardium.

To treat a patient's outer myocardial wall with injections of cultured cells, myocyte micro-granules, medicines and the like, the cradle apparatus 2 is introduced into position around the ventricular walls of the heart 14 in the manner described above. While this is being done, the bladder 44 is in a deflated, non-pressurized state. Once the cradle 12 is in the desired position, the bladder 40 is inflated by pressurizing it with a suitable fluid, such as saline solution. As the bladder 40 inflates, the outer bladder walls 42 press up against the spring arms 18 and are restrained against further outward movement. This forces the inner bladder walls 44 to expand inwardly until the injection needles pierce the myocardial wall and enter the myocardium. At this point, a material to be delivered can be sent through the injection tube 52 and disbursed through the injection needles 50. This is shown in FIG. 10, with the injected material being designated by reference numeral 60. FIGS. 11 and 12 show the continuation and completion of the injection process, respectively. Once the injection process is complete, the bladder 40 is de-pressurized. This causes the bladder 40 to deflate and the injection needles 50 to retract away from the myocardium, as shown in FIG. 13. The cradle 12 may then be withdrawn, as shown in FIG. 14.

As an alternative to injection of a material 60, it should be understood that the cradle apparatus 2 could be modified so that the injection needles 50 are configured as spray nozzles for spraying a material, such as cultured myocyte cells, onto the outer myocardial wall. Prior to spraying, the injection needles could also be used to abrade the outer myocardial wall to increase the likelihood of incorporation of the sprayed material into the myocardium. In addition, or in the alternative, adhesion molecules could first be sprayed onto the outer myocardial wall.

4. Inflatable Cradle for Myocardial Treatment Via Endocardial Approach

Turning now to FIGS. 15–21, an alternative cradle assembly 70 can be constructed for transarterial introduction into a patient's left ventricle or coronary arterial blood vessel. In this embodiment, the cradle assembly 70 is similar in construction to the cradle assembly 2 except that the cradle 12 and the spring arms 18 are replaced with an inflatable balloon cradle 72. The balloon cradle 72 mounts to the end of a lumen (not shown) which may be similar in design and construction to the lumen 14, but must be flexible enough to facilitate its manipulation into the left ventricle or a coronary arterial blood vessel. Like the cradle 12, the balloon cradle 72 can be twisted and compacted for introduction into an introducer 74, which may be similar in design and construction to the introducer 4, but must be flexible enough and suitably sized to facilitate its introduction to the desired location. A system of injection needles 76 is also provided. This system may be identical in design and construction to the system of injection needles 50 described above.

Figure 15:
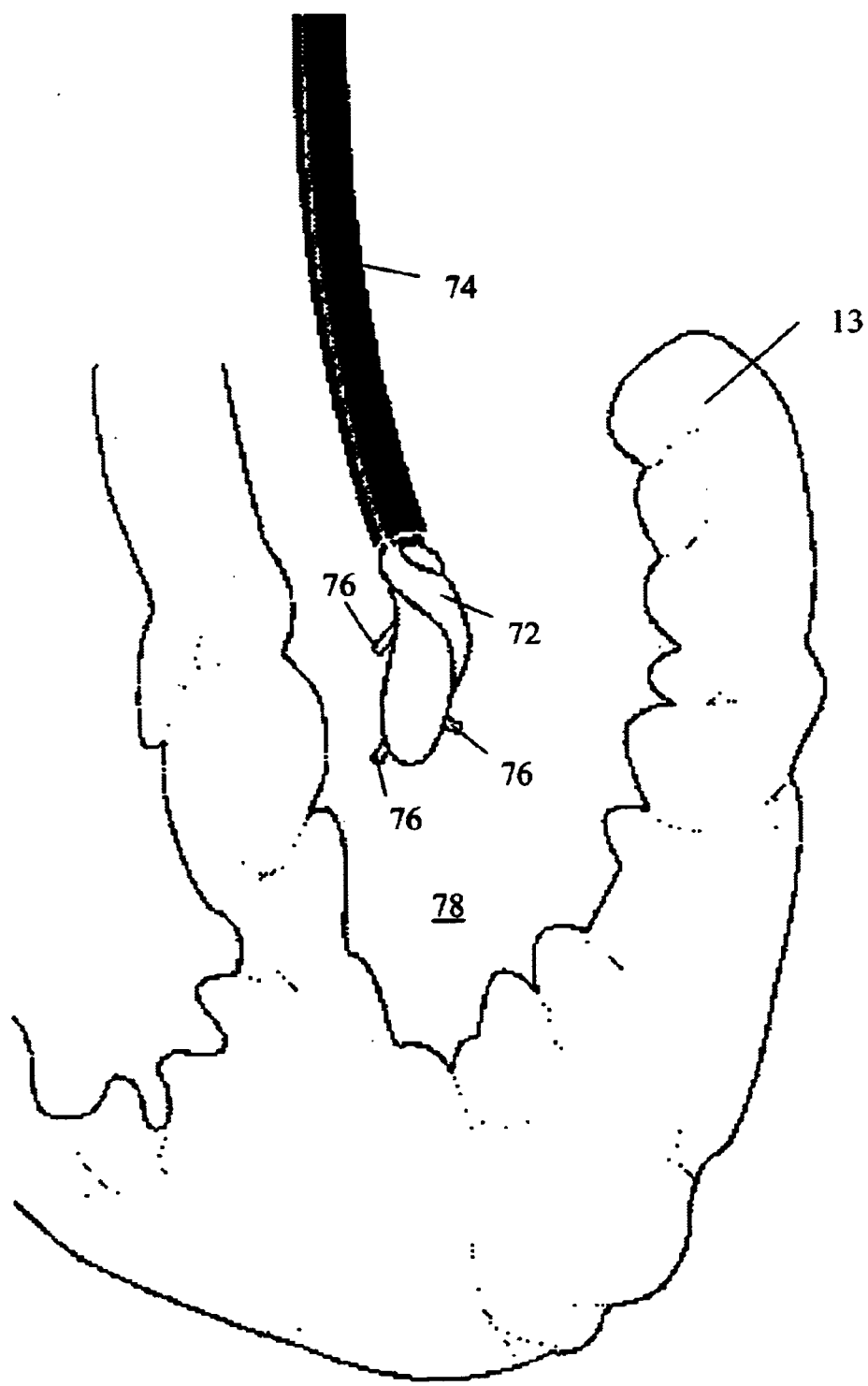
FIG. 15 is a partial cross-sectional view of a patient's heart showing introduction using a transfemoral approach of an inflatable cradle apparatus constructed in accordance with a third embodiment of the invention, with the cradle beginning its emergence from the end of an introducer located in the left ventricle.
Figure 16:
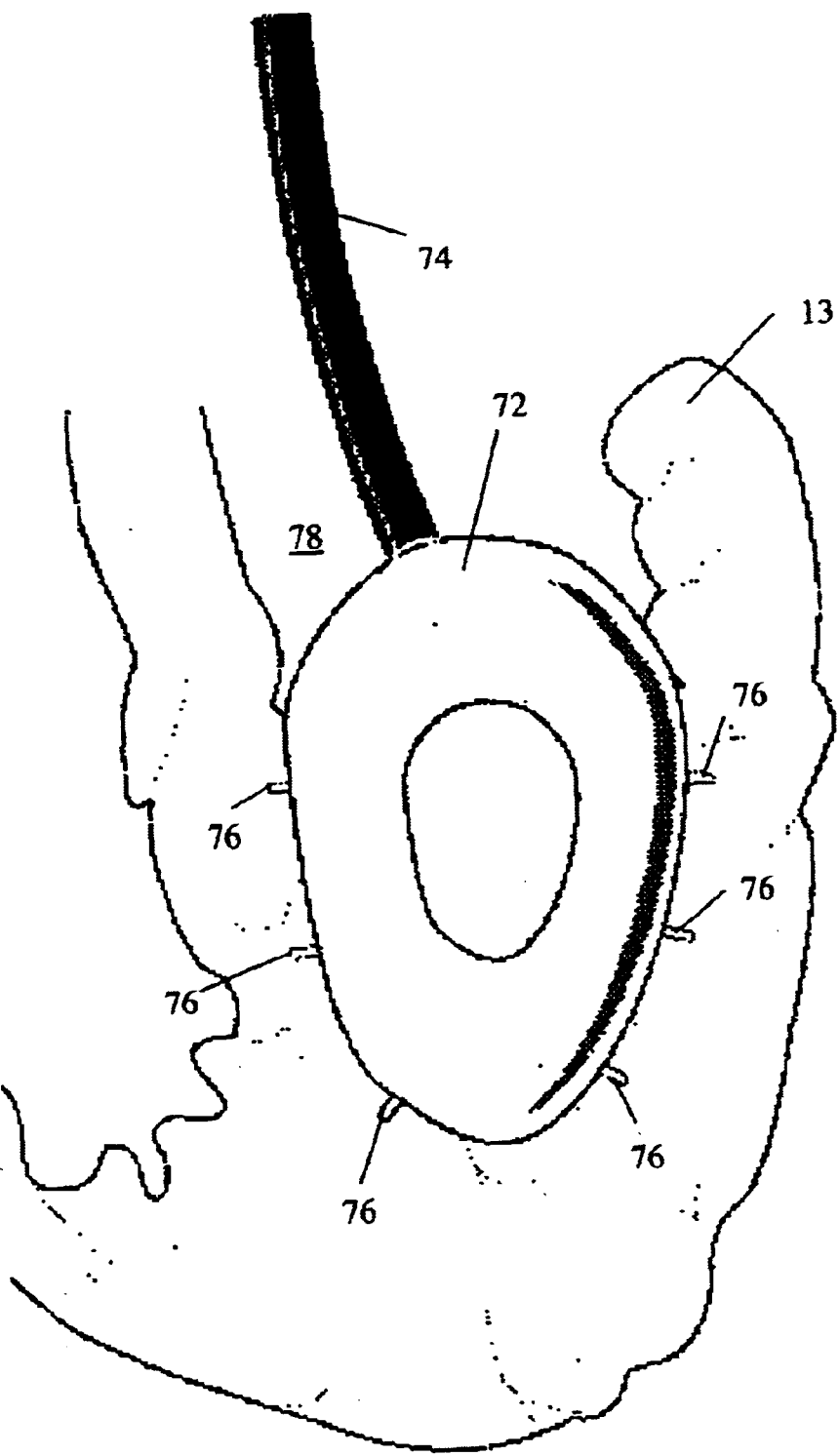
FIG. 16 is a partial cross-sectional view similar to FIG. 15 but showing the cradle fully inflated and equipped with injection needles that have entered the myocardium via the endocardium.
Figure 17:
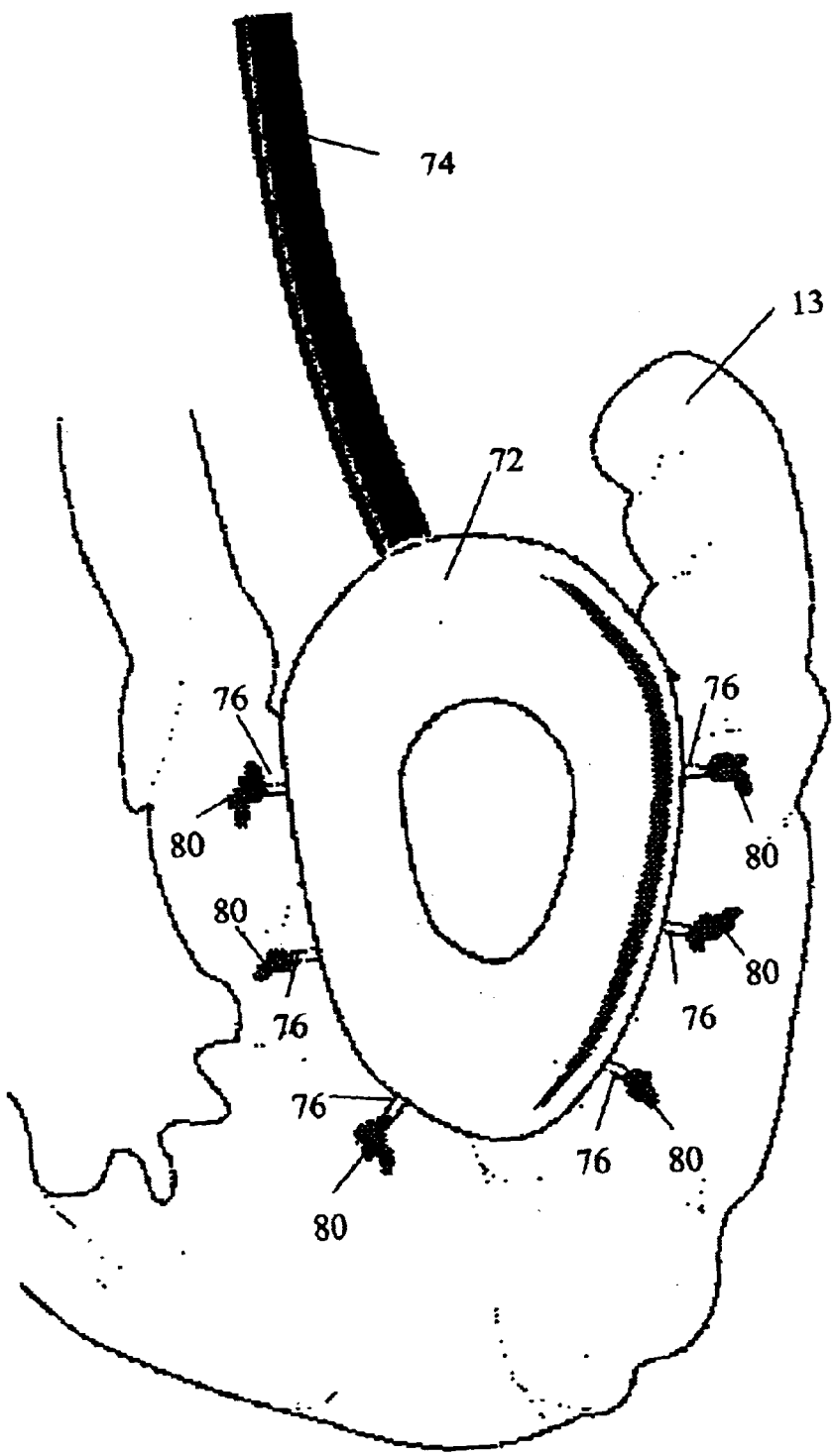
FIG. 17 is a partial cross-sectional view similar to FIG. 15 but showing the injection of material into the myocardium.
Figure 18:
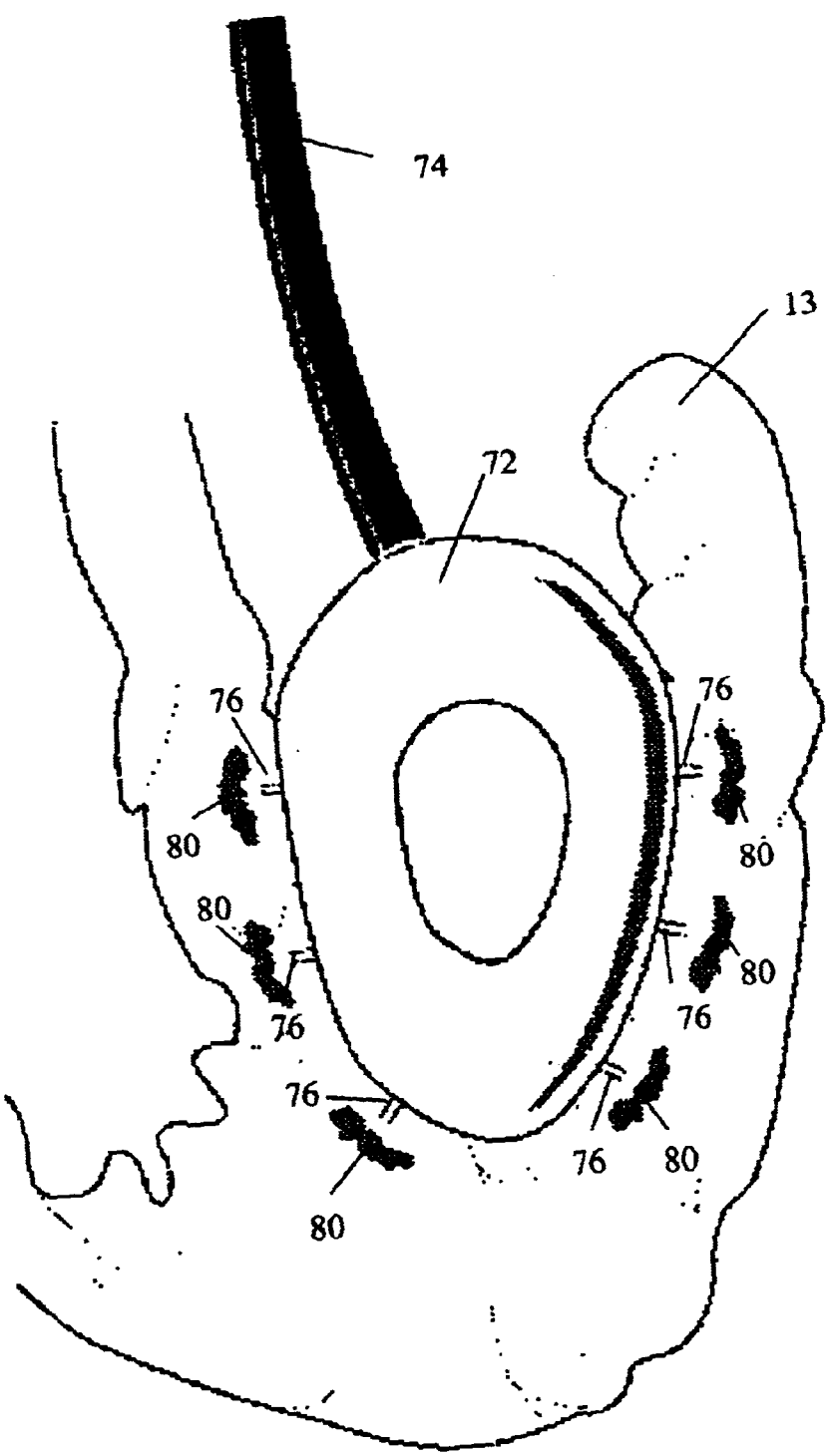
FIG. 18 is a partial cross-sectional view similar to FIG. 15 but showing completion of the injection of material into the myocardium.
Figure 19:
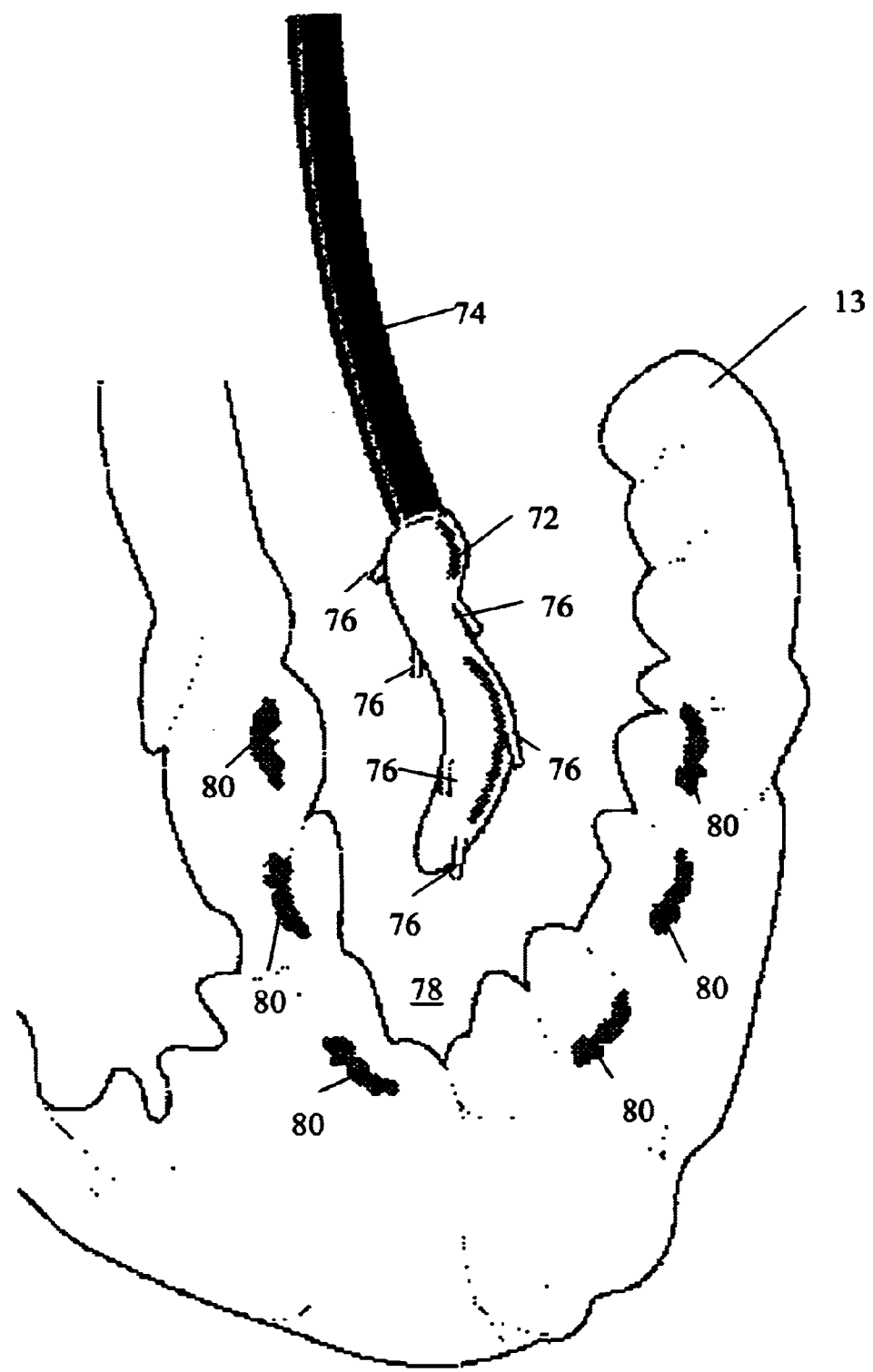
FIG. 19 is a partial cross-sectional view similar to FIG. 15 but showing initial retraction of the now deflated cradle into the introducer following the injection of material into the myocardium.
Figure 20:
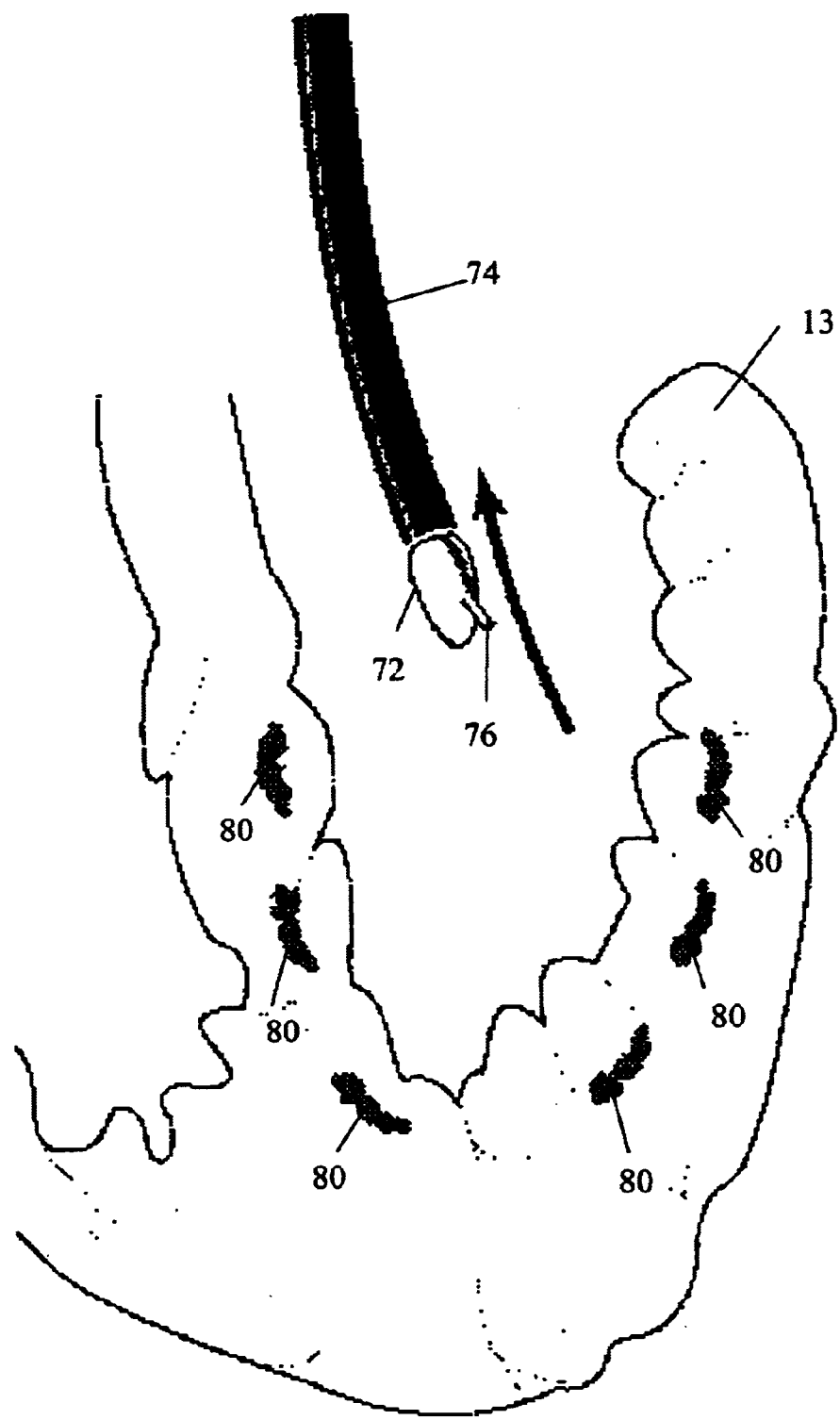
FIG. 20 is a partial cross-sectional view similar to FIG. 15 but showing advanced retraction of the deflated cradle into the introducer.
Figure 21:
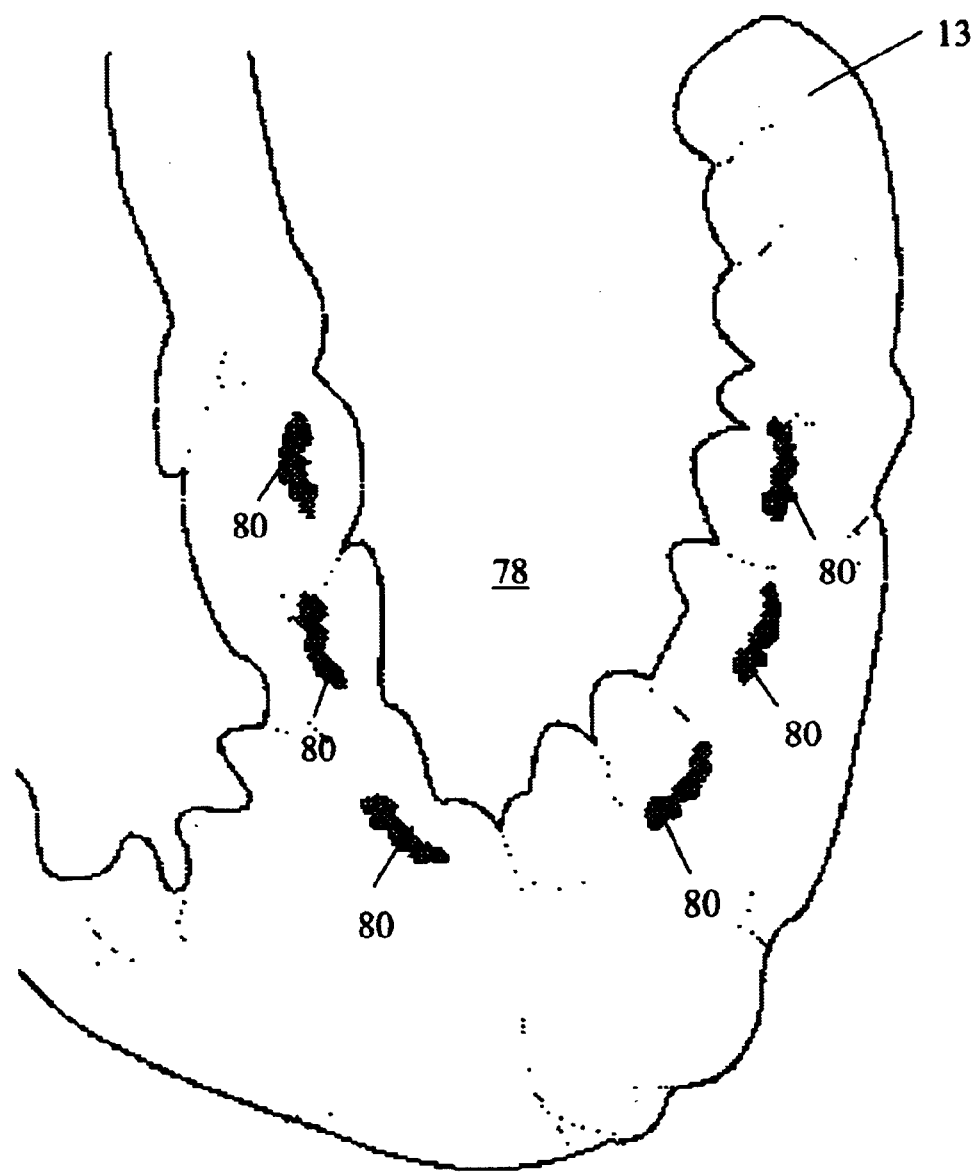
FIG. 21 is a partial cross-sectional view similar to FIG. 15 showing injected material remaining in the myocardium following withdrawal of the introducer.

FIG. 15 shows the balloon cradle 72 as it emerges from the end of the introducer 74 and into a patient's left ventricle 78. In FIG. 16, the balloon cradle is fully inflated with a saline solution or the like, and the injection needles 76 have entered the myocardium via the endocardium. In FIG. 17, the injection needles 76 have begun their injection of a treatment material 80 into the myocardium. As described above, this material could include cultured cells, myocyte micro-granules, medicines, or the like. FIG. 18 shows the completion of material injection into the myocardium. FIG. 19 shows the now-deflated balloon cradle 72 being retracted into the introducer 74, and FIG. 20 shows the completion of this retraction. In FIG. 21, the balloon cradle 72 and introducer 74 have been completely removed from the left ventricle 78, leaving behind the injected material 80 that has been placed into the myocardium. Note that a similar procedure would be used when introducing a material (such as stem cells) into a coronary arterial wall.

5. Combination Myocardial Treatment Via Endocardial and Pericardial Approaches

Figure 22:
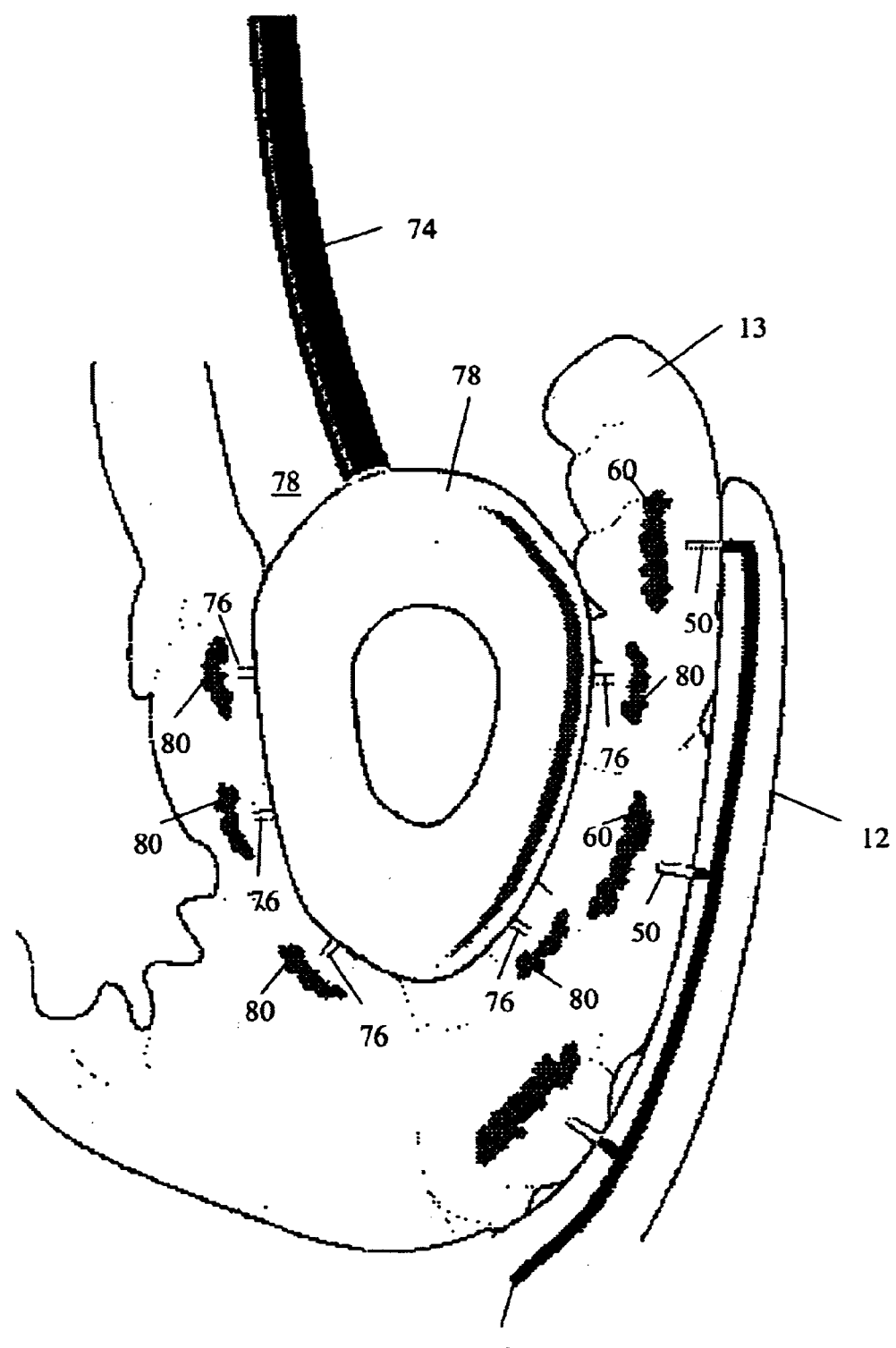
FIG. 22 is a partial cross-sectional view showing injection of material into a myocardium using a combination of an inflatable cradle constructed according to the second embodiment of the invention and an inflatable cradle constructed according to the third embodiment of the invention.

Turning now to FIG. 22, the cradles 12 and 72 can be used in mutual combination to respectively inject the materials 60 and 80 into the myocardium during a single procedure. The materials 60 and 80 could be the same, or they may be different.

Accordingly, an apparatus and methods for cradle-assisted myocardial repair and treatment have been disclosed. Advantages of the disclosed apparatus and method over prior art techniques have been noted. In addition, it should be pointed out that the various apparatus described herein are portable and disposable, making them easy to deploy in a variety of settings, including out-patient facilities. While various embodiments of the invention have been described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A cradle apparatus for myocardial repair and treatment, comprising:

a cradle having a base end, a terminal end, and an intermediate wall portion adapted to apply a myocardial repair or treatment material to a dysfunctional myocardium;

means on said wall portion for applying a treatment material to a myocardium;

a lumen adapted to carry said cradle; and whereby said cradle apparatus can be compacted into a percutaneous or transarterial introducer and then expanded upon emergence from said introducer to engage a ventricular wall of a heart.

2. A cradle apparatus in accordance with claim 1 wherein said cradle is configured as a prosthesis for holding said treatment material against a myocardium, said cradle being removably attached to said spring arms.

3. A cradle apparatus in accordance with claim 1 wherein said cradle apparatus includes a plurality of spring arms mounted to said lumen and attached to said terminal end of said cradle, said spring arms being biased to apply an opening force to said open end of said cradle.

4. A cradle apparatus in accordance with claim 3 wherein said spring arms are metal.

5. A cradle apparatus for myocardial repair and treatment, comprising:

a cradle having a base end, a terminal end, and an intermediate wall portion adapted to apply a myocardial repair or treatment material to a dysfunctional myocardium;

a lumen adapted to carry said cradle;

whereby said cradle apparatus can be compacted into a percutaneous or transarterial introducer and then expanded upon emergence from said introducer to engage a ventricular wall of a heart; and wherein said cradle apparatus is adapted to be twisted and compacted inside a generally tubular introducer.

6. A cradle apparatus for myocardial repair and treatment, comprising:

a cradle having a base end, a terminal end, and an intermediate wall portion adapted to apply a myocardial repair or treatment material to a dysfunctional myocardium;

a lumen adapted to carry said cradle;

whereby said cradle apparatus van be compacted into a percutaneous or transarterial introducer and then expanded upon emergence from said introducer to engage a ventricular wall of a heart; and wherein said lumen is adapted to receive one or more instruments.

7. A cradle apparatus in accordance with claim 6 further including a suction cup mounted to a hydraulic sheath extending through said lumen.

* * * * *